(12) United States Patent
Vanapalli et al.

(10) Patent No.: US 10,209,171 B2
(45) Date of Patent: Feb. 19, 2019

(54) SMART PHONE BASED MULTIPLEXED VISCOMETER FOR HIGH THROUGHPUT ANALYSIS OF FLUIDS

(71) Applicant: Texas Tech University System, Lubbock, TX (US)

(72) Inventors: Siva A. Vanapalli, Lubbock, TX (US); Deepak E. Solomon, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 15/102,918

(22) PCT Filed: Dec. 9, 2014

(86) PCT No.: PCT/US2014/069204
§ 371 (c)(1),
(2) Date: Jun. 9, 2016

(87) PCT Pub. No.: WO2015/089004
PCT Pub. Date: Jun. 18, 2015

(65) Prior Publication Data
US 2016/0305864 A1   Oct. 20, 2016

Related U.S. Application Data (60) Provisional application No. 61/913,607, filed on Dec. 9, 2013.

(51) Int. Cl.
*G01N 11/04* (2006.01)
*G01N 11/06* (2006.01)
(Continued)

(52) U.S. Cl.
CPC ............ *G01N 11/04* (2013.01); *G01N 11/06* (2013.01); *G06T 7/20* (2013.01); *G01N 2011/008* (2013.01); *G06T 2207/10016* (2013.01)

(58) Field of Classification Search
CPC .. G01N 11/04; G01N 11/06; G01N 2011/008; G06T 7/20; G06T 2207/10016
See application file for complete search history.

(56) References Cited

U.S. PATENT DOCUMENTS 4,942,189 A * 7/1990 Peiffer ................. C08J 3/005
523/337
5,489,480 A * 2/1996 Usuki ................... G11B 5/725
427/127
(Continued)

FOREIGN PATENT DOCUMENTS

CN     101750515 A     6/2010
EP     0620432 A1     10/1994
(Continued)

OTHER PUBLICATIONS

Cito et al.,"Visualization and measurement of capillary-driven blood flow using spectral domain optical coherence tomography", Microfluid Nanofluidics. Published Sep. 2012. pp. 23.*
(Continued)

*Primary Examiner* — Mekonen Bekele
(74) *Attorney, Agent, or Firm* — Daniel J. Chalker; Edwin S. Flores; Chalker Flores, LLP (57) ABSTRACT

The present invention includes a method and an apparatus for determining the viscosity of a fluid. The apparatus comprising that includes a microchannel connected to a glass capillary in fluid communication with the microchannel, a digital camera positioned with respect to the glass capillary to capture two or more images of a fluidic slug as a fluid travels within the glass capillary, and a processor (Continued)

communicably coupled to the digital camera that determines a viscosity of the fluid based on the two or more digital images.

30 Claims, 6 Drawing Sheets

(51) Int. Cl.
*G06T 7/20* (2017.01)
*G01N 11/00* (2006.01)

(56) References Cited

U.S. PATENT DOCUMENTS

| | | | |
|---|---|---|---|
| 7,019,834 B2* | 3/2006 | Sebok | G01N 15/147 356/335 |
| 2007/0144967 A1* | 6/2007 | Guenther | B01D 17/045 210/634 |
| 2007/0246076 A1 | 10/2007 | Hafeman | |
| 2010/0005866 A1* | 1/2010 | Sebok | G01F 1/7086 73/54.43 |
| 2010/0136544 A1* | 6/2010 | Agresti | B01F 13/0062 435/287.2 |
| 2011/0237895 A1* | 9/2011 | Yoshida | A61B 1/00009 600/180 |
| 2012/0010465 A1* | 1/2012 | Erikawa | A61B 1/05 600/109 |
| 2012/0096929 A1 | 4/2012 | Baek | |
| 2014/0103556 A1* | 4/2014 | Diaz de Leon Izquierdo | D01D 4/02 264/14 |
| 2014/0316722 A1* | 10/2014 | Szabo | G01N 13/02 702/50 |

FOREIGN PATENT DOCUMENTS

| | | |
|---|---|---|
| EP | 2219020 A1 | 6/2009 |
| KR | 20020095145 A | 12/2002 |
| KR | 20110038351 A | 4/2011 |
| WO | 2015089004 A1 | 6/2015 |

OTHER PUBLICATIONS

Will, J.C., Hernández et al', Automated Measurement of Viscosity with Ubbelohde Viscometers, Camera Unit and Image Processing Software,Simposio de Metrología 2008, pp. 5.*
Bail; Image Processing on a Mobile Platform; University of Manchester—School of Computer Science (2009) Academia.edu.
Buchmann, S., Main cosmetic vehicles, in Handbook of Cosmetic Science and Technology, A.O. Barel, M. Paye, and H.I. Maibach, Editors. 2001, Marcel Dekker, Inc.: New York. p. 145-171.
Choi, S. and J.K. Park, Microfluidic Rheometer for Characterization of Protein Unfolding and Aggregation in Microflows. Small, 2010. 6(12): p. 1306-1310.
Livak-Dahl, E., J. Lee, and M.A. Burns, Nanoliter droplet viscometer with additive free operation. Lab on a Chip, 2013. 13(2): p. 297-301.
Finlayson-Pitts, B.J., et al., The heterogeneous hydrolysis of NO2 in laboratory systems and in outdoor and indoor atmospheres: An integrated mechanism. Physical Chemistry Chemical Physics, 2003. 5(2): p. 223-242.
Galambos, P. and F. Forster, An Optical Microfluidic Viscosmeter. ASME Int. Mech.Eng.Cong.&Exp., 1998. 66: p. 187-191.
Gallegos, D., et al., Label-free biodetection using a smartphone. Lab on a Chip, 2013. 13: p. 2124-2132.
Guillot, P., et al., Viscosimeter on a microfluidic chip. Langmuir, 2006. 22: p. 6438-6445.
Lee, J. and A. Tripathi, Intrinsic viscosity of polymers and biopolymers measured by microchip. Analytical Chemistry, 2005. 77(22): p. 7137-7147.
Lin, H.-W., et al., The Rheological Behaviors of Screening Pastes. Journal of Materials Processing Technology, 2008. 197: p. 136-144.
Mark, D., F.v. Stetten, and R. Zengerle, Microfluidic Apps for off-the-shelf instruments. Lab on a Chip, 2012. 12: p. 2464-2468.
Moon, et al.; Multi-sample micro-slit rheometry; Journal of Rheology, vol. 52 (2008) pp. 1131-1142.
Moon, D. and K.B. Migler, Measurement of dynamic capillary pressure and viscosity via the multi-sample micro-slit rheometer. Chemical Engineering Science, 2009. 64(22): p. 4537-4542.
Pan, L. and P.E. Arratia, A high-shear, low Reynolds number microfluidic rheometer. Microfluidics and Nanofluidics, 2012(1613-4982).
Pipe, C. J. and T. S. Majmudar, High shear rate viscometry. Rheologica Acta, 2008.47: p. 621-642.
Rao, M.A., Rheology of Fluid and Semisolid Foods: Principles and Applications. Food Engineering Series. 2007, New York: Springer.
Santoyo, E., et al., Rheological property measurement of drilling fluids used in geothermal wells. Applied Thermal Engineering, 2001. 21: p. 283-302.
Srivastava, N. et al., Burns Nanoliter viscometer for analyzing blood plasma and other liquid samples. Analytical Chemistry, 2005. 77: p. 383-392.
Vargaftik, N.B., et al., International Tables of the Surface-Tension of Water. Journal of Physical and Chemical Reference Data, 1983. 12(3): p. 817-820.
Wilkes, J.O., Fluid Mechanics for Chemical Engineers. 2005, New Jersey: Prentice Hall International Series.
Xia, Y.N. and G.M. Whitesides, Soft lithography. Angewandte Chemie-International Edition, 1998. 37(5): p. 551-575.
Solomon, D. E. and S. A. Vanapalli, iCapillary: A smartphone based microfluidic viscometer pp. 1-21.
Extended European Search Report, EP 14869207.2 dated Aug. 29, 2017.

* cited by examiner

SMART PHONE BASED MULTIPLEXED VISCOMETER FOR HIGH THROUGHPUT ANALYSIS OF FLUIDS

CROSS REFERENCE TO RELATED APPLICATIONS

This application claims priority to, and is the National Phase of International Application No. PCT/US2014/069204, filed on Dec. 9, 2014, which claims the benefit under 35 U.S.C. § 119(e) of U.S. Provisional Application No. 61/913,607, filed Dec. 9, 2013. All of which are hereby incorporated by reference in their entirety.

TECHNICAL FIELD OF THE INVENTION

The present invention relates generally to the field of viscometers and, more particularly, to viscometers for high throughput analysis of fluids.

BACKGROUND ART

Viscometers are an important tool in characterizing the rheological properties of products in industries such as food processing [1], consumer products [2], inks [3], polymers [4], drilling fluids [5] and lubricants [6]. In most of these industries, there is often a need to quickly characterize viscosity of one or more samples at the location where products are being made or processed, rather than being shipped offsite. Mechanical rheometers although capable of performing a broad suite of precise rheological measurements are not well suited for such onsite or field viscometry applications, because of their bulkiness and need for skilled operators. Viscosity measurement devices such as Saybolt, capillary tube and rotational viscometers are more suited for onsite usage because of their non-complicated operation and cost effectiveness. Although handy, these devices have a number of limitations which include (i) use of large sample volumes (ii) cumbersome cleaning procedures if multiple sample measurements are needed (iii) limited shear rate range and (iv) the presence of non-viscometric flow kinematics (e.g. Saybolt viscometer) making it difficult to interpret viscosity data for complex fluids.

In the last decade, microfluidic viscometers [7-13, 17] have emerged as alternative tools capable of addressing the above limitations of conventional viscometers. Microfluidic viscometers developed to date use a variety of driving sources to introduce fluid flow in microchannels. In some cases constant fluid flow rate is imposed using syringe pumps [7, 10-12], in other cases constant pressure drop is delivered using pressure sources [13] or capillary pressure gradients [9]. Knowing the relation between pressure drop and flow rate, the viscosity of the fluid is determined. In these devices, depending on the driving force, the fluid response is measured using pressure sensors embedded on the channel surface [7, 12] or image-based detection of fluid interfaces [8-10, 13, 14, 17].

Despite several microfluidic viscometers being reported in the literature, current devices have some limitations. For example, in pressure-sensor based viscometers because the sensing is coupled to fluid flow, they are not ideal for handling clinical samples where use-and-throw capability is desired to avoid sample cross-contamination. Likewise, repeated handling of industrial-grade particulate fluids in these devices may become problematic due to adhesion of particles on channel and sensor surfaces, unless rigorous washing protocols are implemented. Finally, pressure-sensor based devices do not scale favorably for parallelized measurements. In contrast, microfluidic viscometers based on imaging sensors have the advantage that the element is un-coupled from fluid flow in the channel. This feature not only allows parallel of multiple samples, but also creates the opportunity to fabricate disposable devices. Current approaches to image-based viscometry rely on the use of research-grade microscopes and cameras, making them only suitable for laboratory environments. However, such approaches are not simple and flexible enough for onsite or field applications in resource-poor settings.

Rheosense has a device in market that uses pressure sensors embedded in microfluidic chips to find viscosity of fluids. Anton Paar and AR instruments have rheometers in the market, which are mechanical in nature and use rotors to imply stress on fluids and calculate the corresponding viscosity.

DISCLOSURE OF THE INVENTION

The invention includes a simple microfluidic viscometer integrated with smartphone technology. A fluid is driven into a microfluidic chip using a constant pressure source. The flow rate of the fluid due to this applied pressure is found by attaching a glass capillary to the outlet of this device and measuring the speed of the fluidic slug as it moves through the capillary. The uncomplicated nature of the device allows the use of smartphones to be used as sensors to find the flowrate of the fluid within the microfluidic chip without the use of pressure sensors or other expensive imaging equipment. Knowing both applied pressure and flowrate the viscosity of any type of fluid can be found. The use of the microfluidic chip allows reaching shear rates unachievable with convention macroscopic rheometers.

The present invention provides a simple microfluidic viscometer integrated with smartphone technology. The method involves driving the fluid into a microchannel at constant pressure, and using the smartphone to track the fluid front in a glass capillary attached to the microchannel. It has been demonstrated that videos of the fluid interface propagation in the capillary can be recorded using the smartphone, transferred wirelessly to a workstation, analyzed quickly, and the viscosity data relayed back to the smartphone device. This 'iCapillary' device measures quantitatively the viscosity of Newtonian and shear-thinning polymeric fluids over a broad range of shear rates (10-10,000 $s^{-1}$). Furthermore, the simplicity of the iCapillary device allows for parallel measurement of viscosity of several samples. Since the sensing element is uncoupled to fluid flow, the present invention offers the potential to create inexpensive use-and-throw devices for on-site viscosity analysis of clinical samples and industrial-grade complex fluids. Finally, the basic approach presented here, can be expanded to integrate specific 'apps' into smartphone technology for on-the-fly analysis and sharing of rheological data for real-time quality control of complex fluids.

The present invention provides an apparatus comprising that includes a microchannel connected to a glass capillary in fluid communication with the microchannel, a digital camera positioned with respect to the glass capillary to capture two or more images of a fluidic slug as a fluid travels within the glass capillary, and a processor communicably coupled to the digital camera that determines a viscosity of the fluid based on the two or more digital images.

In addition, the present invention provides a method of determining a viscosity of a fluid using a digital camera by providing an apparatus that includes a microchannel connected to a glass capillary in fluid communication with the microchannel, and a digital camera positioned with respect to the glass capillary to capture two or more images of the fluid within the glass capillary. The fluid is introduced into the microchannel and the digital camera captures two or more digital images of a fluidic slug as the fluid travels within the glass capillary. The viscosity of the fluid is then determined based on the two or more digital images.

In one embodiment, the present invention provides an apparatus that includes a microchannel connected to a glass capillary in fluid communication with the microchannel, a digital camera positioned with respect to the glass capillary to capture two or more images of a fluidic slug as a fluid travels within the glass capillary, and a processor communicably coupled to the digital camera that determines a viscosity of the fluid based on the two or more digital images. In one aspect, the microfluidic channel is fabricated using soft lithography technique. In another the microfluidic channel having a width (w) of 100 to 1000 µm, a height (h) of 50 to 100 µm and length (Lch) of 1 to 2 cm. In another aspect, the microfluidic channel having a hydrodynamic resistance that accounts for more than 85% of the total resistance in the glass capillary. In aspect, the glass capillary having an inner radius of 0.375 to 1 mm and length of 5 to 10 cm. In another aspect, the apparatus further comprises a hydrostatic head or fluidic controller connected to the microchannel that applies one or more different driving pressures to the microchannel. In another aspect, a video capture rate of the digital camera is set to a time taken for the fluidic slug travel a minimum distance of 1 cm in the glass capillary. In another aspect, a resolution of the digital camera is set to at least 100 pixels/cm. In another aspect, one or more digital images captured by the digital camera are transferred from the processor to an image-processing workstation using a wireless area network. In another aspect, the processor further detects a location of the fluidic slug within the microcapillary using an automated algorithm. In another aspect, the processor further cropping the two or more digital images to have only the capillary the field of view, applying a threshold to the two or more digital images, detecting two or more edges in the two or more digital images to identify a contour of the fluidic slug, and applying a Hough transform to the edges of the fluidic slug to determine a length of the fluidic slug. In another aspect, both polar and non-polar solvent viscosity can be measured. In another aspect, apparatus performs viscosity measurements on multiple samples simultaneously. In another aspect, the processor integrated into the digital camera or wirelessly connected to the digital camera. In another aspect, the apparatus further comprises a smartphone, a tablet, a personal digital device, a computer pad, a netbook, or a computer having digital camera integrated In another embodiment, the present invention includes a method of determining a viscosity of a fluid using a digital camera by providing an apparatus having a microchannel connected to a capillary in fluid communication with the microchannel, and the digital camera positioned with respect to the glass capillary to capture two or more images of the fluid within the glass introducing the fluid into the microchannel; capturing the two or more digital images of a fluidic slug as the fluid travels within the glass capillary, and determining the viscosity and shear rate of the fluid based on the two or more digital images and applied pressure drop. In another aspect, microfluidic channel is fabricated using soft lithography technique. In another aspect, the microfluidic channel having a width (w) of 100 to 1000 µm, a height (h) of 50 to 100 µm and a length (Lch) of 1 to 2 cm. In another aspect, the microfluidic channel having a hydrodynamic resistance that accounts for more than 85% of a total resistance in the glass capillary. In another aspect, the glass capillary having an inner radius of 0.375 to 1 mm and length of 5 to 10 cm. In another aspect, the method further comprises the step of applying one or more different driving pressures to the microchannel are applied using a hydrostatic head connected to the In another aspect, the method further includes setting a video capture of the digital camera to a time taken for the fluidic slug to travel a minimum distance of 1 cm in the glass capillary. In another aspect, the method further includes setting a resolution of the digital camera to 100 pixels/cm. In another aspect, the method further includes transferring the two or more digital images to an image-processing workstation using a wireless area network. In another aspect, the method further includes detecting a location of the fluidic slug within the microcapillary using automated algorithm. In another aspect, the method further includes cropping the two or more digital images to have only the capillary in the field of view, applying a threshold to the two or more digital images, detecting two or more edges in the two or more digital images to identify a contour of the fluidic slug, and applying a Hough transform to the edges of the fluidic slug to determine a length of the fluidic slug. In another aspect, both polar and non-polar solvent viscosity can be measured. In another aspect, the method is used to perform viscosity measurements on multiple samples simultaneously.

The present invention is described in detail below with reference to the accompanying drawings.

DESCRIPTION OF THE DRAWINGS

The above and further advantages of the invention may be better understood by referring to the following description in conjunction with the accompanying drawings, in which.

DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention. The discussion herein relates primarily to the design and simulation of ladder networks, but it will be understood that the concepts of the present invention are applicable to viscometers.

To facilitate the understanding of this invention, a number of terms are defined below. Terms defined herein have meanings as commonly understood by a person of ordinary skill in the areas relevant to the present invention. Note that these terms may be used interchangeable without limiting the scope of the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention provides viscometer for determining viscosity in industries such as food processing, consumer products, inks, polymers, drilling fluids, deicing fluids and lubricants. The viscosity determination can be made in a multiplexed manner for industries that require "on-field" or in-line viscosity determination. Novel and unusual features include, but are not limited to: (1) use of a capillary attached to a microfluidic chip to serve as a sensor for flowrate measurement; and (2) use of a smartphone as a sensing element coupled with the sensor to find viscosity from flow rate.

The present invention has all the advantages of microfluidic viscometers such as the product from Rheosense, which include viscosity determination at very high shear rates. Significant advantages over the viscometers in market are: (1) the present invention can operate in most rugged and resource sparse field environments with only a smartphone required for finding viscosity; (2) multiple sample viscosity can be determined at the same time increasing throughput and efficiency without a corresponding increase in number of sensing elements (smartphones in this case); and (3) the present invention however does not use pressure sensors which are expensive to dispose of after single use for applications that deal with fluids that are difficult to remove from the chip such as industrial grade suspensions and colloids. The present invention can be a "use and throw device".

Viscosity determination requires calibration in the beginning of a measurement. This can be overcome by either knowing the surface tension of the fluid or by having an electronically controlled pressure source for compensating the laplace pressure in the glass capillary.

Figure 1A:
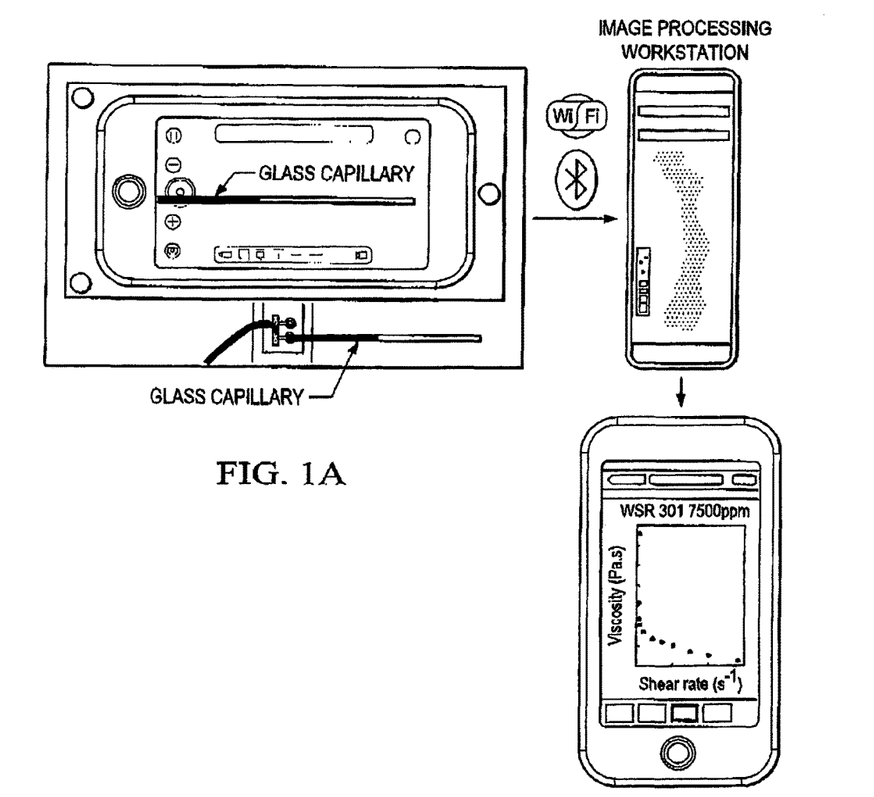
FIG. 1A is an illustration of the operation cycle of an iCapillary viscometer.

Recently, there has been significant interest in integrating smartphone-based imaging into microfluidic applications [15, 16]. Current smartphones contain cameras capable of recording images at 30 frames per second in 720 pixels of vertical resolution (720p). This video-recording capability provides significant opportunities for inexpensive visualization of complex fluid flows in microfludic devices. For example, as shown in FIG. 1A, the smartphone acquires images of the fluid front motion in the glass capillary (i.e., fluid flows relevant for viscometry are visualized), and the videos are transferred wirelessly to the workstation for processing. The results can be subsequently accessed on the smartphone. Since smartphones have the capability to transfer files wirelessly at rates greater than 1 Mbps, hundreds of images can be transferred quickly, analyzed on the workstation and the results relayed back to the smartphone as shown in FIG. 1A. Moreover, the ubiquitous presence of these devices in both laboratories and field settings allows for real time quality control of fluid rheology. Finally, specific 'apps' can be developed allowing on-the-fly data analysis, logging and sharing that is especially crucial for applications where a large number of samples are processed in a day.

The present invention exploits the basic features of smartphones as image sensors to measure the viscosity of fluids using a microchannel coupled to a glass capillary. This device is referred to as "iCapillary". The method relies on imposing a constant pressure drop and measuring the flow rate by monitoring a slug (i.e., air-fluid interface) propagation in the glass capillary using the smart phone (see FIG. 1B). Prior image-based viscometry methods [10, 17] use co-flowing laminar streams to determine viscosity, which require high quality imaging sensors and optics to determine the interface location. Moreover, the co-flowing laminar streams approach might have problems in measuring the viscosity of complex fluids that contain components that are partially miscible in polar and non-polar solvents. The device and method of the present invention is devoid of such issues. Importantly, the simplicity and portability of our method offers the potential for onsite viscometry as well as disposable devices. The present invention can be extended to perform viscosity measurements on multiple samples simultaneously increasing operational efficiency.

Figure 1B:
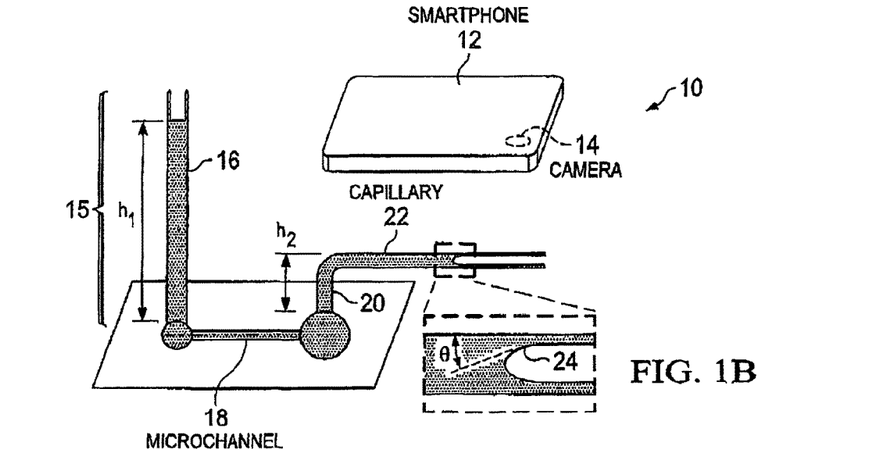
FIG. 1B is a close-up view of an iCapillary viscometer, showing the microchannel, the connected glass capillary and the smartphone.

A close-up view of the device (iCapillary viscometer) is represented in FIG. 1B showing the microchannel, the connected glass capillary and the smartphone. The bottom right shows the zoomed-in view of the air-fluid interface for a wettable glass capillary. FIG. 1B shows an iCapillary device 10 of the present invention that can use, e.g., a smartphone 12 that includes a camera 14 capable of taking multiple images of the fluidics 15 of the device. A known pressure head 16 ($h_1$) is applied to drive a fluid into a microchannel 18 of width (w), height (h) length ($L_{ch}$). As shown in this example, the volumetric flow rate (Q) (see insert 24) of the fluid in the microchannel 18 is determined by measuring the mean velocity of the slug in the attached capillary 22 using the in-built camera 14 in the smartphone 12. The mean velocity of a slug is multiplied by the cross-sectional area of the glass capillary 22 to obtain the volumetric flow rate.

The viscosity and shear rate for Newtonian and non-Newtonian fluids can be computed from the data captured. Briefly, the analysis presented here is an example in which the fluidic resistance in the glass capillary and the tubing associated with the hydrostatic head are negligible. In the setup used these contributions are non-negligible, and were accounted for as discussed in great detail herein below.

The viscosity for a Newtonian fluid is given by, $$\mu = \frac{\rho g \Delta h + P_L}{QS} \tag{1}$$

where ρ is the density of the fluid, g is the acceleration due to gravity, Δh is the differential hydrostatic head ($h_1$-$h_2$, see FIG. 1b), $P_L$ is the Laplace pressure due to the curvature of the air-liquid interface and S is the geometric factor that incorporates all the different conduits (and their dimensions) present in the iCapillary device. A detailed derivation of Equation (1) and the method for determining $P_L$ is presented hereinbelow. All the parameters in Equation (1) are known from studies, enabling quantification of viscosity of the fluid.

For a 2D microchannel, where w>>h, the wall shear rate for the Newtonian fluid can be estimated as, $$\gamma_o = \frac{6Q}{wh^2} \quad (2)$$

For non-Newtonian fluids, the wall shear rate prescribed by Equation (2) needs to be modified to account for the non-parabolic velocity profile characteristic of complex fluids. The Weissenberg-Rabinowitch-Mooney analysis developed for a slit rheometer [18] was used to obtain the 'true' wall shear rate for the non-Newtonian fluid as, $$\dot{\gamma} = \frac{\dot{\gamma}_o}{3}\left(2 + \frac{d(\ln \dot{\gamma}_o)}{d(\ln \tau_w)}\right) \quad (3)$$

where the wall shear stress ($\tau_w$) is determined from the imposed pressure drop as $$\tau_w = \frac{(\rho g \Delta h + P_L)wh}{2L_{ch}(w+h)} \quad (4)$$

Finally, the viscosity of a non-Newtonian fluid is given by $$\mu = \frac{\tau_w}{\dot{\gamma}} \quad (5)$$

Thus, Equations (2)-(5) can be used to compute the viscosity versus shear rate curve for a non-non-Newtonian fluid, under the assumptions of negligible pressure drop in the glass capillary the tubing. Calculate $d(\ln \dot{\gamma}_o)/d(\ln \tau_w)$ by fitting a polynomial to the data. For the fluids used this study, it was found that fitting a second order polynomial provides sufficient accuracy.

A flowchart for operation of the iCapillary device is depicted in FIG. 1A. In brief, the images are first captured using the smartphone (iPod, Apple Inc, Cupertino, Calif.) followed by transferring the video files to the image processing workstation. After the images are processed the results are viewed on Matlab Mobile (which is installed on the iPod).

The device includes a microfluidic channel fabricated using soft lithography technique [19], with a width (w) of 1000 μm, height (h) of ≈60 μm and length ($L_{ch}$) of 0.44 cm. The hydrodynamic resistance encountered by the fluid in the microchannel accounts for more than 85% of the total resistance in the device (see Table 1 herein below). The outlet of the microfluidic device is connected to a glass capillary having an inner radius of 0.375 mm and length of 8 cm.

The following protocol was used for conducting the viscosity studies. Different driving pressures are applied using a hydrostatic head and the resulting motion of the fluidic slug is captured using a smartphone. To manipulate the frame rate and format for video capturing, a third party application (ProCAM, iTunes Store) was used. The movies were recorded in VGA file format at 15 frames per second. To minimize errors in flow rate measurements the duration of the video capture is set to the time taken for the fluidic slug to travel a minimum distance of 1 cm in the glass capillary. This distance translates to nearly 100 pixels, yielding an error of 2% in the detection of the air-slug interface. The entire movie for all the driving pressures is then transferred to an image-processing workstation using a wireless area network.

The transferred video files are then analyzed on the workstation using Matlab (Mathworks, Boston, Mass.). Typical size of the video files recorded range from 8-100 MB with data transfer rates of 1-2 Mbps. An automated algorithm detects the location of the fluidic slug in the capillary. Briefly, the image is first cropped to have only the capillary in the field of view, a threshold is applied on the images, followed by edge detect to find the contours of the fluidic slug. Finally, a Hough transform is applied to the edges of the slug to determine the length of the fluidic slug. Typical processing time on the server is 1 min for a single a viscosity measurement. For each viscosity data point about 10 frames were analyzed to compute slug velocity.

Figure 2A:
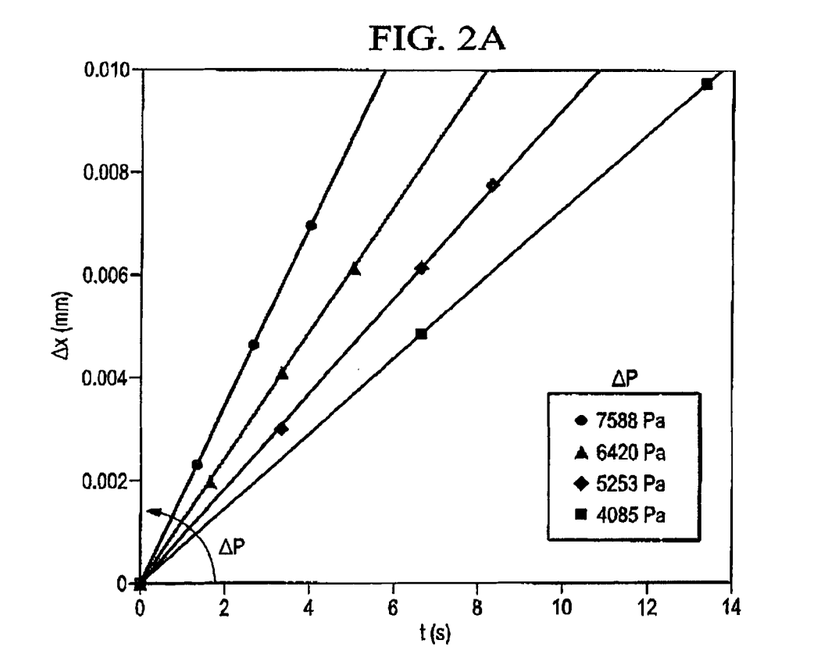
FIG. 2A shows the time-evolution of the propagation of the fluid front in the glass capillary at different driving pressures (DP)

It was first verified whether for a given fluid viscosity, the slug in the capillary moves at a constant velocity. FIG. 2A shows the time-evolution of the propagation of the fluid front in the glass capillary at different driving pressures (DP). The fluid is glycerol solution of viscosity 55 mPa·s. The lines are linear fits to the experimental data. As shown in FIG. 2A, all the pressure drops tested, the interface moves linearly with time, implying that the fluidic slug is moving at a constant velocity. This observation indicates that contact-line pinning and dewetting issues were negligible for the fluids (Newtonian and polymeric solutions) tested.

Figure 2B:
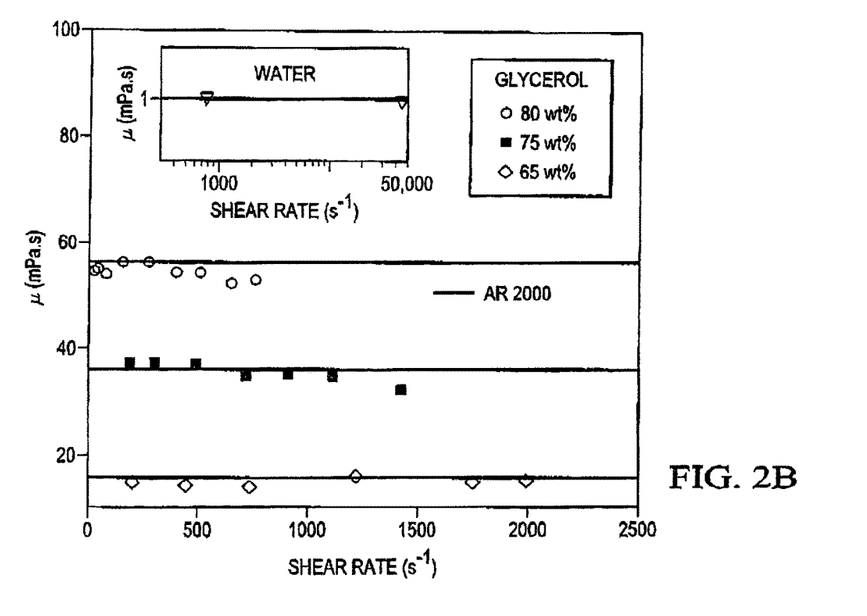
FIG. 2B shows the viscosity as a function of shear rate for three different glycerol solutions as measured by the iCapillary (symbols)

To demonstrate the capability of the iCapillary device for measuring viscosity tested Newtonian fluids were tested first. Three different glycerol solutions having a viscosity range between ~15-55 mPa·s were chosen. FIG. 2B shows the viscosity as a function of shear rate for three different glycerol solutions as measured by the iCapillary (symbols). The mean viscosity value obtained from the rheometer (AR2000) is shown as lines. The inset shows the viscosity data for water at high shear rates, as measured by the iCapillary device. As shown in FIG. 2B, the viscosity values obtained from the iCapillary for the different fluids were compared with the data obtained from a mechanical rheometer (AR2000, TA Instruments, New Castle, Del.). The data from the microfluidic viscometer were in good agreement with that from the rheometer. The iCapillary used less than 1 mL of fluid to acquire viscosity data over a shear rate range between ~10-1000 $s^{-1}$. Much higher shear rates can also be accessed at the cost of larger sample volumes. For example, the inset of FIG. 2B shows that the shear rate range can be expanded to as high as 40,000 $s^{-1}$ for water-like fluids. For the current device configuration and fluids like water, 40000 $s^{-1}$ was the maximum accessible shear rate, which was dictated by the maximum speed of image acquisition (30 fps) available on the smart phone. Opportunities exist to access even higher shear rates by using a higher diameter capillary tube and employing non-deformable microfluidic chips. In most applications, the shear rate range demonstrated by our iCapillary device is sufficient.

Figure 3:
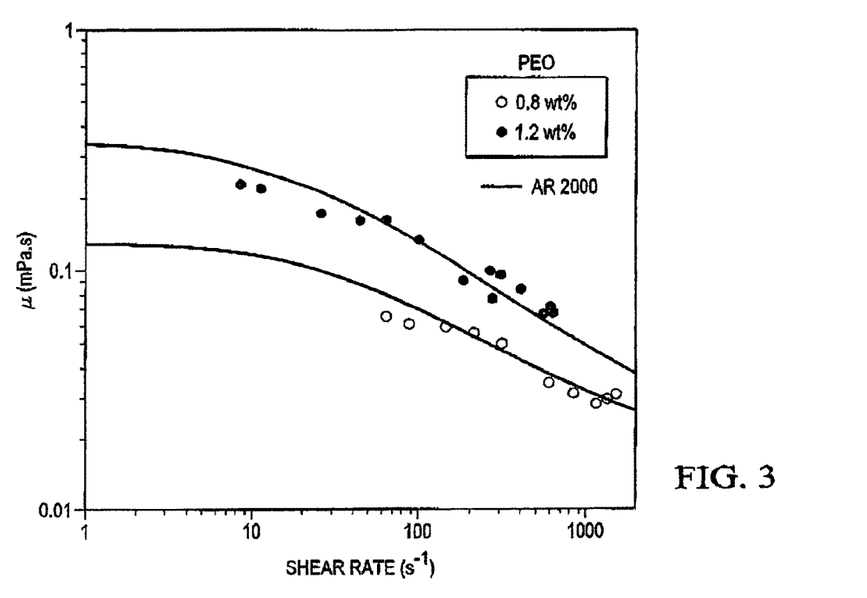
FIG. 3 shows the viscosity of polymeric fluids measured as a function of shear rate by the iCapillary device (symbols) and the rheometer (lines)

Next, the capability of the iCapillary to measure the viscosity of polymeric fluids having a shear-shear-rate dependent viscosity was assessed. Polyethylene oxide (PEO) fluids having an approximate molecular weight of 2×106 g/mol (WSR-N60K, DOW, Midland, Mich.) were chosen the model fluid. Two different concentrations of 0.8 and 1.2 wt % were tested. FIG. 3 shows the measured viscosities of these polymeric fluids as a function of shear rate using the iCapillary device and their comparison with viscosities obtained from the mechanical rheometer. The data in good agreement indicating that the iCapillary device can also measure the viscosity curves for non-Newtonian fluids.

Figure 4A:
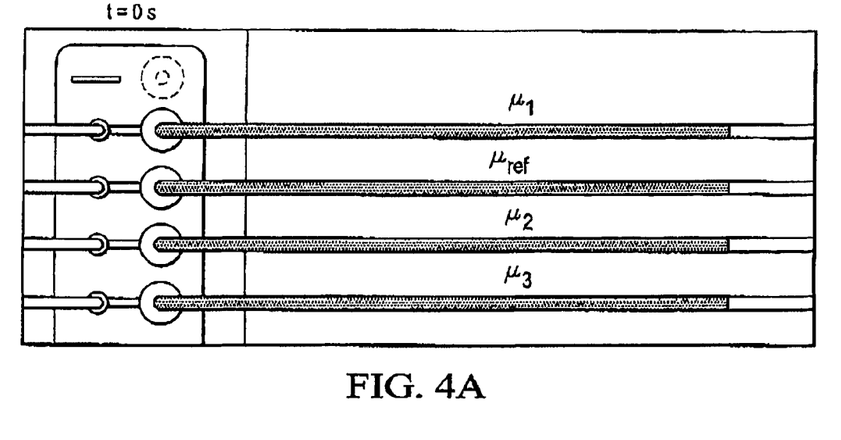
FIG. 4A is an image showing that the fluid front of the three samples (denoted by $\mu_1$, $\mu_2$, $\mu_3$) and the reference fluid (denoted by $\mu_{ref}$) are at the same relative position at t=0.
Figure 4B:
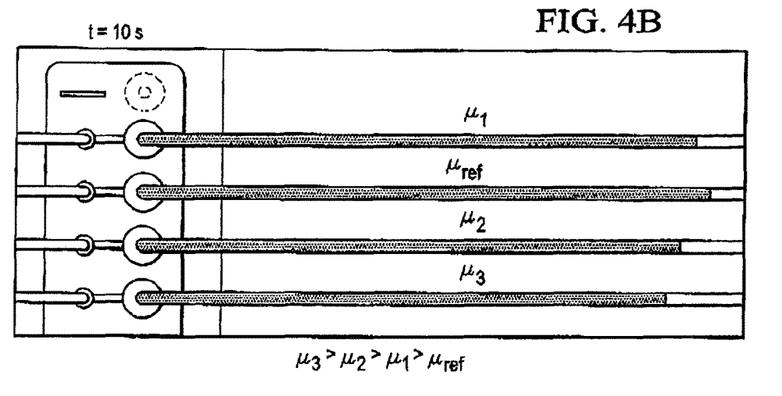
FIG. 4B shows that when a constant driving pressure is applied, the fluid fronts in all the samples moves a distance that is inversely proportional to their viscosities.
Figure 4C:
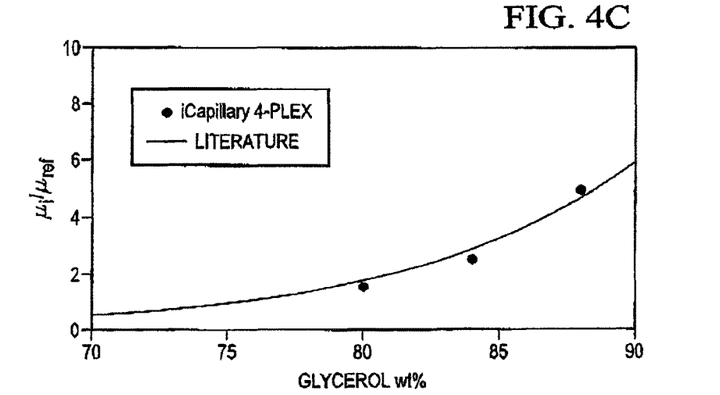
FIG. 4C shows the relative viscosity of the three different samples determined from the iCapillary viscometer (symbols) are in good agreement with those obtained from literature (lines)

The simplicity of this approach involving a microchannel and a connected glass capillary also allows parallelized measurements of viscosity of multiple samples. FIGS. 4A to 4C show multiplexed viscosity measurements using a reference fluid. FIG. 4A is an image showing that the fluid front of the three samples (denoted by $\mu_1$, $\mu_2$, $\mu_3$) and the reference fluid (denoted by $\mu_{ref}$) are at the same relative position at t=0. As shown in FIG. 4A, several glass capillaries can be connected to a single molded device containing multiple microchannels. This multiplexed viscometry capability is desirable if a large number of samples need to be tested on a regular basis. There are two routes in which the iCapillary device can be operated for simultaneous measurement of viscosity of several samples. In the first route, a single video recording can be taken for samples flowing through the set of capillaries for a specified duration. The resulting images can be analyzed and the viscosity curves for multiple samples can be obtained. This approach is a logical extension of the single iCapillary device approach to multiple samples, which is not described in detail here.

Another route involves measuring the viscosity of multiple samples compared to a reference sample of known viscosity. This comparative viscometry method not only simplifies the data analysis on multiple samples tremendously (discussed below), but also might be more practically relevant. For example, comparative viscometry can be used to assess batch-to-batch variations in a product or alternatively to determine if the product quality has changed due to repeated usage (e.g. ink formulations and lubricants) and prolonged storage (e.g. consumer and food products).

Comparative viscometry can be implemented on the iCapillary device. If the applied pressure drop and channel dimensions are the same, and the two fluids are tracked for the same duration, the ratio of viscosities between the reference and 'test' fluids is then inversely proportional to the ratio of the distance traversed by the test and reference fluids (Equation 6).

$$\frac{\mu_1}{\mu_2} = \frac{d_2}{d_1} \quad (6)$$

It is thus possible to estimate differences in viscosity between the reference and several test fluids by simply knowing the relative distances moved by the fluidic slugs in a given time interval. In a similar way the shear rate of the sample fluid can also be calculated knowing the shear rate of the test fluid since $$\frac{\dot{\gamma}_1}{\dot{\gamma}_2} = \frac{d_1}{d_2} \quad (7)$$

This comparative analysis can be applied to both Newtonian and rheologically similar non-Newtonian fluids provided that the magnitude and duration of applied pressure is the same.

The capability of the iCapillary to perform comparative viscosity analysis was demonstrated by taking four different Newtonian fluids in the viscosity range of 35-150 mPa·s. The fluid with viscosity of 35 mPa·s was selected as the reference sample, and determines the viscosity of the other three fluids from the iCapillary device by comparing the relative distances moved by the respective fluidic slugs. FIG. 4A and FIG. 4B shows the snapshot of the location of the four fluid slugs at t=0 and 10 s respectively. Visual inspection of the images immediately allows one to gauge the ranking of the viscosity of the four different fluids. Thus, by injecting all the samples at the same time, the device provides a simple means to qualitatively assess the differences in the viscosity of several samples simultaneously.

In situations, where a quantitative measurement is desired, images can be processed off-line. FIG. 4C quantifies the off-line results obtained from the iCapillary compared against the literature values. The measurement data is in good agreement with literature values with the percentage of viscosity deviation being less than 5%. The time taken for the measurement was less than a minute for three samples, and less than 0.1 ml of sample volumes were used. The number of samples that can be tested simultaneously is only be limited by the field of view of the camera in the smart phone. For the smartphone used in this study it is estimated that it can simultaneously image ~30 capillaries. Thus, this simple method has the potential to determine viscosity curves for a large number of samples in parallel, profoundly saving time and manpower.

Figure 5:
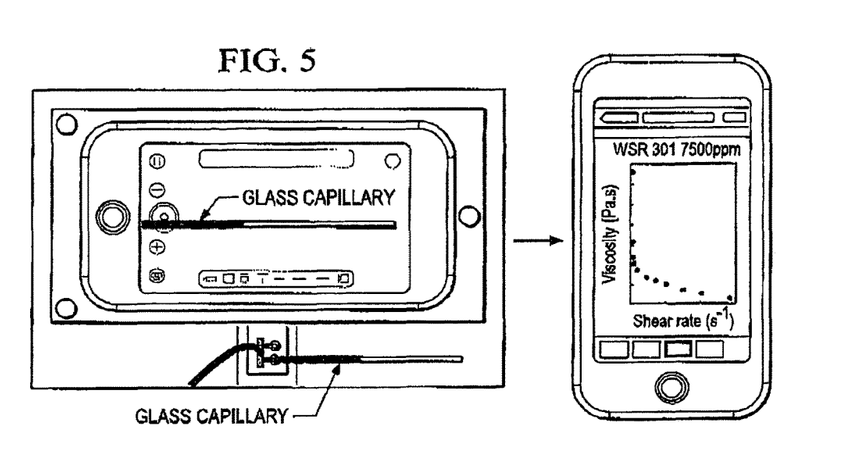
FIG. 5 shows a microfluidic viscometry of complex fluids using smartphone technology.

The present invention includes a portable smartphone based microfluidic viscometer which is capable of quantifying the viscosity curves for both Newtonian and non-Newtonian fluids. For example, FIG. 5 shows a microfluidic viscometry of complex fluids using smartphone technology. Pressure drop versus flow rate relationship is determined by recording fluid front motion in a glass capillary connected to a microchannel. To collect viscosity data over a shear range of 10-1000 s$^{-1}$ currently requires about 1 mL of sample, 20 mins of experimentation time and another 40 mins of off-line data analysis. This throughput is comparable to conventional rheometers. However, unlike conventional rheometers, which serially process samples, the iCapillary device can process samples in parallel using a comparative method. In this case, the iCapillary device outperforms the rheometer since all the samples can be delivered using a single pressure source, and because several capillaries are captured on an image, only a single video need to be processed for quantifying viscosity of multiple samples.

The basic platform demonstrated here could be further improved. Instead of hydrostatic head, fluid delivery can be finely controlled using electronic pressure regulators. Specific 'apps' can be designed that will allow image and data analysis on the smartphone itself, rather than transferring files to workstation. Both the microchannel and glass capillary can be fabricated into a single unit using technologies such as 3D printing. With these additional improvements, our device offers significant potential for onsite viscometry and in applications that desire disposable devices.

Figure 6:
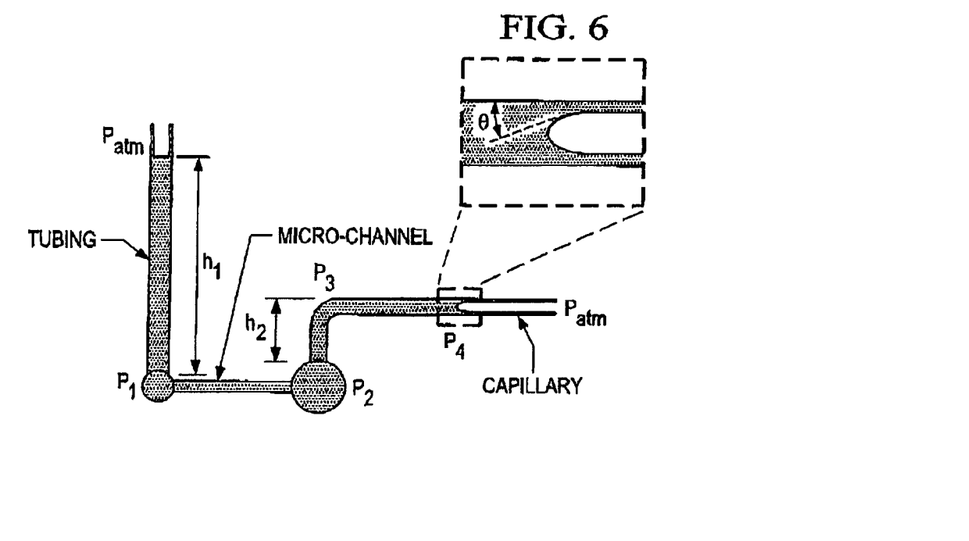
FIG. 6 shows a schematic diagram of the iCapillary device.

To calculate the viscosity for a Newtonian fluid, a resistive network approach similar to electrical circuits is used, where the relation between pressure drop and flow rate is specified using the analogy of Ohm's law. A schematic representation of the iCapillary device is shown in FIG. 6, which also depicts the pressures at different sections of the device. The top right illustration shows the magnified view of the air-fluid interface having a contact angle, θ, with the wettable surface (i.e. glass capillary in the experiment). The pressure drop of a fluid flowing through a conduit can be determined from the product of the hydrodynamic resistance of the fluid (R) and the volumetric flow rate (Q). The hydrodynamic resistance is a function of fluid viscosity and conduit dimensions.

The fluid first flows from a hydrostatic column at height $h_1$ through the tubing to reach the inlet of the microchannel. The pressure drop across the tubing is given by Equation 8, $$P_{atm} - P_1 + \rho g h_1 = Q R_t \tag{8}$$

where $\rho g h_1$ is the hydrostatic pressure contribution from a fluid of density ρ. Rt is the hydrodynamic resistance of the fluid in the tubing which is given by $8 \mu L / \pi R^4$. Here μ is the fluid viscosity, R is the radius of the tubing (0.635 mm) and Lt is the length of tubing (≤1.5 m).

The fluid then flows through the rectangular microchannel of length $L_{ch}$, width w and height h, generating pressure drop, $P_1$-$P_2$, given by Equation (9).

$$P_1 - P_2 = Q R_{ch} \tag{9}$$

In Equation (9), $R_{ch}$ is the hydrodynamic resistance of the fluid in the microchannel, which is given by $12 \mu L_{ch}/wh^3$ for channel aspect ratios much smaller than 1 (which is h/w=0.06 in our device).

A glass capillary having a vertical height of $h_2$ (=6 mm) and radius, r (=0.375 mm) is connected to the outlet of the microchannel. The pressure drop from the outlet of the microchannel through the vertical section of the glass capillary (shown in FIG. 6) is given as $$P_2 - P_3 + \rho g h_2 = Q R_{gc1} \tag{10}$$

where $R_{gc1}$ (=$8 \mu h_2/\pi r^4$) denotes the hydrodynamic resistance of the fluid in the vertical portion of the glass capillary.

The hydrodynamic resistance of the fluid in the horizontal section of the glass capillary is depicted as $R_{gc2} = 8 \mu L_{gc}/\pi r^4$, where $L_{gc}$ is the slug length in the capillary. The pressure drop across this section is given by, $$P_3 - P_4 = Q R_{gc2} \tag{11}$$

Finally, the pressure drop due to the Laplace pressure ($P_L$) across the curved air-liquid interface is given by, $$P_{atm} - P_4 = P_L = \frac{2\sigma \cos \theta}{r} \tag{12}$$

where σ is the surface tension between the fluid-air interface, θ is the contact angle between the fluid and the glass capillary.

Summing Equation 7-12 yields, $$\rho g(h_1 - h_2) + P_L = Q(R_t + R_{ch} + R_{gc1} + R_{gc2}) \tag{13}$$

Equation (13) can be re-written as $$\rho g \Delta h + P_L = \mu Q S \tag{14}$$

where $\Delta h = h_1 - h_2$ and S is a geometric factor given by $$S = \frac{8 L_t}{\pi R^4} + \frac{12 L_{ch}}{w h^3} + \frac{8 h_2}{\pi r^4} + \frac{8 L_{gc}}{\pi r^4} \tag{15}$$

Thus, the relation for viscosity of the fluid can be rewritten from Equation (15) as, $$\mu = \frac{\rho g \Delta h + P_L}{Q S} \tag{16}$$

Equation (16) is the central equation that has been used to determine the viscosity of the Newtonian fluids used these studies. In Equation (16), all the quantities are known from the experiment except $P_L$. $P_L$ was empirically determined by tuning the head (Δh) such that flow is nominally zero. In that case, $P_L$ is simply given by −ρgΔh (see Equation (13), note that the hydrostatic head $h_1$ needs to be lowered below $h_2$, making Δh<0). It was verified that for water the fluid, this approach yields a value of $\Delta P_L \approx 391$ Pa, which is in good agreement with the determined from known surface tension of water (σ=72.75 mN/m [1]) and its contact angle glass (θ=25° [2]). For fluids in which interfacial properties are known, the Laplace pressure contribution can be determined from Equation (12). Alternatively, the empirical approach can be used to determine $\Delta P_L$. The contribution of $\Delta P_L$ becomes insignificant when viscosity is being measured at high shear rates because under these conditions $\rho g \Delta h \gg \Delta P_L$.

The geometric factor S describes the relative contribution of different sections of the device towards the total hydrodynamic resistance of the fluid ($R_{total}$). In these studies, the hydrodynamic resistance from tubing and the glass capillary contributes a small fraction to the overall fluidic resistance in the iCapillary as shown in Table 1.

TABLE 1

Calculated hydrodynamic resistance of the various sections in the iCapillary device, normalized with the total resistance ($R_{total}$) in the device.

| Component | $R/R_{total} \times 100$ |
|---|---|
| $R_t$ (tubing) | <10% |
| $R_{ch}$ (microchannel) | >85% |
| $R_{gc1}$ (capillary-vertical section) | <1% |
| $R_{gc2}$ (capillary-horizontal section) | <4% |

Assuming a 2D microchannel, the wall shear rate for a Newtonian fluid can be determined from $$\dot{\gamma}_o = \frac{6Q}{wh^2} \tag{17}$$

In the case of shear-thinning polymeric fluids the above analysis (for Newtonian fluids) needs to be modified to account for the non-parabolic velocity profile in the microchannel. The Weissenberg-Rabinowitch-Mooney analysis developed for a slit rheometer can be used to obtain the 'true' wall shear rate as:

$$\dot{\gamma} = \frac{\dot{\gamma}_o}{3}\left(2 + \frac{d(\ln \dot{\gamma}_o)}{d(\ln \tau_w)}\right) \tag{18}$$

In Equation (18) $\tau_w$ is the wall shear stress in the microchannel. If the pressure drop ($P_1$-$P_2$) across the microchannel (see FIG. 6) is known then force balance on a fluid element gives the wall shear stress as $$\tau_w = \frac{(P_1 + P_2)wh}{2L_{ch}(w+h)} \quad (19)$$

In principle by knowing the flow rate (Q) and pressure drop ($P_1-P_2$), the true shear rate can be calculated by using Equations (18) and (19). Moreover, the viscosity of the polymeric fluid can then be determined as $$\mu = \frac{\tau_w}{\dot{\gamma}} \quad (20)$$

In the iCapillary device, if the fluidic resistance due to tubing and the glass capillary are ignored then $$P_1 - P_2 = \rho g \Delta h + P_L \quad (21)$$

It was found that using Equation (21) as an estimate for the pressure drop across the microchannel the viscosity values from the iCapillary device deviated from the rheometer data by up to 20%. This significant deviation implies that the flow resistance in the tubing and the glass capillary needs to be taken into account.

Figure 7:
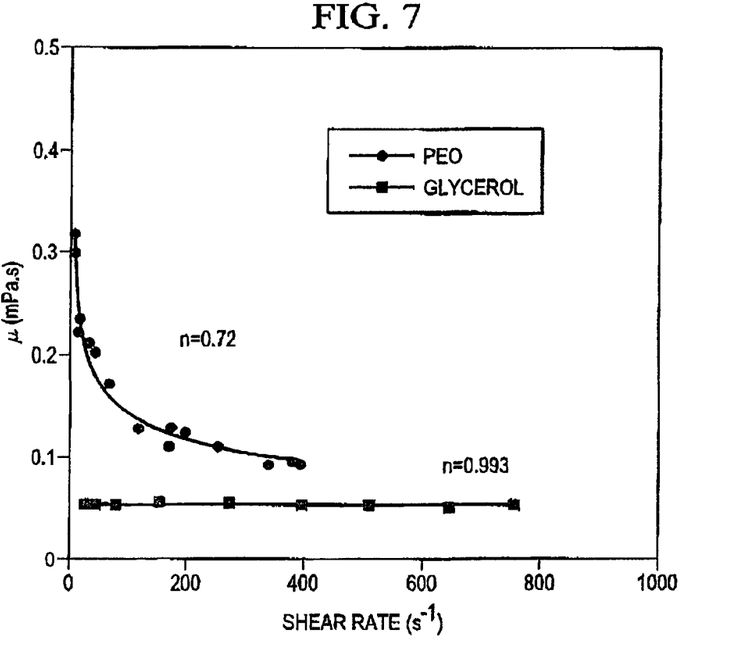
FIG. 7 is a graph with the power law index for Newtonian Glycerol and non-Newtonian PEO solutions.

For non-Newtonian fluids, because the viscosity depends on shear rate, the viscosity of the fluid in the tubing and glass capillary can be quite different from that in the microchannel. As a result, without a piori knowledge of the functional dependence of viscosity on shear rate, it is difficult to directly compensate for the contributions of tubing and glass capillary to the total fluidic resistance. To proceed further, it was assumed that the polymeric fluids obey power-law rheology [3] of the form $$\mu = K(\dot{\gamma})^{n-1} \quad (22)$$

where K is the consistency index and n is the power law index which is <1 for shear thinning polymeric fluids. To obtain the values of K and n, use Equations (17-21). FIG. 7 shows the values of n obtained using this approach for PEO and Newtonian fluid. The value of n obtained from the rheometer data for the same PEO solution is 0.69, which is in good agreement with our estimate. These fit values were used to determine the fluidic resistances of the tubing and glass capillary due to the shear-thinning nature of the fluid. Such a compensation allows one to obtain good agreement with the rheometer data as shown in FIG. 3.

It will be understood that particular embodiments described herein are shown by way of illustration and not as limitations of the invention. The principal features of this invention can employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

It will be understood by those of skill in the art that information and signals may be represented using any of a variety of different technologies and techniques (e.g., data, instructions, information, signals, bits, symbols, and chips may be represented by voltages, currents, electromagnetic waves, magnetic fields or particles, optical fields or particles, or any thereof). Likewise, the various illustrative logical blocks, modules, circuits, and algorithm steps described herein may be implemented as electronic hardware, computer software, or of both, depending on the application and functionality. Moreover, the various logical blocks, modules, and circuits described herein may be implemented or performed with a general purpose processor (e.g., microprocessor, conventional processor, controller, microcontroller, state machine or combination of computing devices), a digital signal processor ("DSP"), an specific integrated circuit ("ASIC"), a field programmable gate array ("FPGA") or other programmable logic device, discrete gate or transistor logic, discrete hardware components, or combination thereof designed to perform the functions described herein. Similarly, steps of a method or process described herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art.

All of the systems, devices, computer programs, compositions and/or methods disclosed and claimed herein can be made and executed without undue experimentation in light of the present disclosure. While the systems, devices, computer programs, compositions and methods of this invention have been described in terms of preferred embodiments, it will be apparent to those of skill in the art that variations may be applied to the systems, devices, computer programs, compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Rao, M. A., Rheology of Fluid and Semisolid Foods: Principles and Applications. Food Engineering Series. 2007, New York: Springer.
2. Buchmann, S., Main cosmetic vehicles, in Handbook of Cosmetic Science and Technology, A. O. Barel, M. Paye, and H. I. Maibach, Editors. 2001, Marcel Dekker, Inc.: New York. p. 145-171.
3. Lin, H.-W., et al., The Rheological Behaviors of Screening Pastes. Journal of Materials Processing Technology, 2008. 197: p. 136-144.
4. Kontopoulou, M., Applied Polymer Rheology:Polymeric Fluids with Industrial Applications 2011, New York: Wiley.
5. Santoyo, E., et al., Rheological property measurement of drilling fluids used in geothermal wells. Applied Thermal Engineering, 2001. 21: p. 283-302.
6. Malimard, J., M. Querry, and P. Vergne, Lubricant rheology in real conditions: measurements and confrontation with a ball/disk contact. Revue de Metallurgie, 2002. 98(02): p. 141-148.
7. C. J. Pipe, T. S. Majmudar, and G. H. McKinley High shear rate viscometry. Rheologica Acta, 2008. 47: p. 621-642.
8. Lee, J. and A. Tripathi, Intrinsic viscosity of polymers and biopolymers measured by microchip. Analytical Chemistry, 2005. 77(22): p. 7137-7147.
9. N. Srivastava, R. D. Davenport, and M. A. Burns Nanoliter viscometer for analyzing blood plasma and other liquid samples. Analytical Chemistry, 2005. 77: p. 383-392.
10. Guillot, P., et al., Viscosimeter on a microfluidic chip. Langmuir, 2006. 22: p. 6438-6445.
11. Galambos, P. and F. Forster, An Optical Microfluidic Viscosmeter. ASME Int. Mech.Eng.Cong.&Exp., 1998. 66: p. 187-191.
12. Pan, L. and P. E. Arratia, A high-shear, low Reynolds number microfluidic rheometer. Microfluidics and Nanofluidics, 2012(1613-4982).
13. Livak-Dahl, E., J. Lee, and M. A. Burns, Nanoliter droplet viscometer with additive free operation. Lab on a Chip, 2013. 13(2): p. 297-301.
14. Moon, D. and K. B. Migler, Measurement of dynamic capillary pressure and viscosity via the multi-sample micro-slit rheometer. Chemical Engineering Science, 2009. 64(22): p. 4537-4542.
15. Mark, D., F. v. Stetten, and R. Zengerle, Microfluidic Apps for off-the-shelf instruments. Lab on a Chip, 2012. 12: p. 2464-2468.
16. Gallegos, D., et al., Label-free biodetection using a smartphone. Lab on a Chip, 2013. 13: p. 2124-2132.
17. Choi, S. and J. K. Park, Microfluidic Rheometer for Characterization of Protein Unfolding and Aggregation in Microflows. Small, 2010. 6(12): p. 1306-1310.
18. Macosko, C. W., Rheology: Principles, Measurements and Applications. 1994, New York: Wiley-VCH.
19. Xia, Y. N. and G. M. Whitesides, Soft lithography. Angewandte Chemie-International Edition, 1998. 37(5): p. 551-575.
20. Vargaftik, N. B., B. N. Volkov, and L. D. Voljak, International Tables of the Surface-Tension of Water. Journal of Physical and Chemical Reference Data, 1983. 12(3): p. 817-820.
21. Finlayson-Pitts, B. J., et al., The heterogeneous hydrolysis of NO2 in laboratory systems and in outdoor and indoor atmospheres: An integrated mechanism. Physical Chemistry Chemical Physics, 2003. 5(2): p. 223-242.
22. Wilkes, J. O., Fluid Mechanics for Chemical Engineers. 2005, New Jersey: Prentice Hall International Series.
23. Moon, et al.; Multi-sample micro-slit rheometry; Journal of Rheology, Vol. 52 (2008) pp. 1131-1142.
24. Srivastava, et al.; Nanoliter Viscometer for Analyzing Blood Plasma and Other Liquid Samples; Analytical Chemistry (2005) Vol. 77 (2), pp. 383-392.
25. Bail; Image Processing on a Mobile Platform; University of Manchester-School of Computer Science (2009) Academia.edu.
26. US Patent Application Publication No. 20120096929.

The invention claimed is:

1. An apparatus comprising:
 a microchannel connected to a glass capillary in fluid communication with the microchannel;
 a pressure source connected to the microchannel that applies a constant pressure to the microchannel;
 a digital camera positioned with respect to the glass capillary to capture two or more images of a fluidic slug as a fluid travels within the glass capillary; and
 a processor communicably coupled to the digital camera that determines a location of the fluidic slug within the glass capillary for each of the two or more digital images, determines a flow rate of the fluid based on the locations of the fluidic slug within the glass capillary and a viscosity of the fluid based on the applied pressure and the flow rate of the fluid.

2. The apparatus of claim 1, wherein the microchannel is fabricated on a microfluidic chip using soft lithography technique.

3. The apparatus of claim 1, the microchannel having a width (w) of 100 to 1000 µm, a height (h) of 50 to 100 µm and a length ($L_{ch}$) of 1 to 2 cm.

4. The apparatus of claim 1, the microchannel having a hydrodynamic resistance that accounts for more than 85% of the total resistance in the glass capillary, the microchannel and a tubing connected to the microchannel.

5. The apparatus of claim 1, the glass capillary having an inner radius of 0.375 to 1 mm and length of 5 to 10 cm.

6. The apparatus of claim 1, wherein the pressure source comprises a hydrostatic head or fluidic controller connected to the microchannel that applies one or more different driving pressures to the microchannel.

7. The apparatus of claim 1, wherein a video capture rate of the digital camera is set to a time taken for the fluidic slug to travel a minimum distance of 1 cm in the glass capillary.

8. The apparatus of claim 1, wherein a resolution of the digital camera is set to at least 100 pixels/cm.

9. The apparatus of claim 1, wherein one or more digital images captured by the digital camera are transferred from the processor to an image-processing workstation using a wireless area network.

10. The apparatus of claim 1, the processor further detecting a location of the fluidic slug within the glass capillary using an automated algorithm.

11. The apparatus of claim 1, the processor further cropping the two or more digital images to have only the capillary in the field of view, applying a threshold to the two or more digital images, detecting edges in the two or more digital images to identify a contour of the fluidic slug, and applying a Hough transform to the edges of the fluidic slug to determine a length of the fluidic slug.

12. The apparatus of claim 1, wherein both polar and non-polar solvent viscosity can be measured.

13. The apparatus of claim 1, wherein:
the microchannel comprises two or more microchannels;
the glass capillary comprise two or more glass capillaries that are parallel to one another;
each microchannel connected to one of the glass capillaries in fluid communication with the microchannel;
the two or more images are of the all the fluidic slugs within the glass capillaries;
the processor determines the viscosity of each fluid in the glass capillaries simultaneously.

14. The apparatus of claim 1, the processor integrated into the digital camera or wirelessly connected to the digital camera.

15. The apparatus of claim 1, wherein the digital camera is integrated into a smartphone, a tablet, a personal digital device, a computer pad, a netbook, or a computer.

16. A method of determining a viscosity of a fluid using a digital camera comprising the steps of:
providing an apparatus comprising:
a microchannel connected to a glass capillary in fluid communication with the microchannel;
a pressure source connected to the microchannel;
the digital camera positioned with respect to the glass capillary to capture two or more images of the fluid within the glass capillary;
introducing the fluid into the microchannel;
applying a constant pressure to the microchannel using the pressure source;
capturing the two or more digital images of a fluidic slug as the fluid travels within the glass capillary using the digital camera; and
determining a location of the fluidic slug within the glass capillary for each of the two or more digital images; and
determining a flow rate of the fluid based on the locations of the fluidic slug within the glass capillary and a viscosity of the fluid based on the applied pressure and the flow rate of the fluid.

17. The method of claim 16, wherein the microchannel is fabricated on a microfluidic chip using soft lithography technique.

18. The method of claim 16, the microchannel having a width (w) of 100 to 1000 μm, a height (h) of 50 to 100 μm and a length ($L_{ch}$) of 1 to 2 cm.

19. The method of claim 16, the microchannel having a hydrodynamic resistance that accounts for more than 85% of a total resistance in the glass capillary, the microchannel and a tubing connected to the microchannel.

20. The method of claim 16, the glass capillary having an inner radius of 0.375 to 1 mm and length of 5 to 10 cm.

21. The method of claim 16, wherein the pressure source comprises a hydrostatic head or fluidic controller applying one or more different driving pressures to the microchannel.

22. The method of claim 16, further comprising the step of setting a video capture of the digital camera to a time taken for the fluidic slug to travel a minimum distance of 1 cm in the glass capillary.

23. The method of claim 16, further comprising the step of setting a resolution of the digital camera to 100 pixels/cm.

24. The method of claim 16, further comprising the step of transferring the two or more digital images to an image-processing workstation using a wireless area network.

25. The method of claim 16, further comprising the step of detecting a location of the fluidic slug within the glass capillary using an automated algorithm.

26. The method of claim 16, further comprising the steps of:
cropping the two or more digital images to have only the capillary in the field of view;
applying a threshold to the two or more digital images,
detecting edges in the two or more digital images to identify a contour of the fluidic slug; and
applying a Hough transform to the edges of the fluidic slug to determine a length of the fluidic slug.

27. The method of claim 16, wherein both polar and non-polar solvent viscosity can be measured.

28. The method of claim 16, wherein:
the microchannel comprises two or more microchannels;
the glass capillary comprise two or more glass capillaries that are parallel to one another;
each microchannel connected to one of the glass capillaries in fluid communication with the microchannel;
the two or more digital images are of the all the fluidic slug within the glass capillaries;
the determination of the viscosity of each fluid in the glass capillaries are performed simultaneously.

29. The apparatus of claim 1, further comprises the processor determining a shear rate of the fluid based on the flow rate and a pressure drop, and providing a graph of the viscosity versus shear rate for the fluid.

30. The method of claim 16, further comprising:
determining a shear rate of the fluid based on the flow rate and a pressure drop; and
providing a graph of the viscosity versus shear rate for the fluid.

* * * * *